(12) United States Patent
Deal

(10) Patent No.: US 8,956,419 B2
(45) Date of Patent: Feb. 17, 2015

(54) OPEN LUMEN STENT

(75) Inventor: Travis Deal, Freedom, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 884 days.

(21) Appl. No.: 12/119,680

(22) Filed: May 13, 2008

(65) Prior Publication Data

US 2008/0288082 A1   Nov. 20, 2008

Related U.S. Application Data

(60) Provisional application No. 60/917,799, filed on May 14, 2007.

(51) Int. Cl.
*A61M 27/00* (2006.01)

(52) U.S. Cl.
CPC .................................... *A61M 27/008* (2013.01)
USPC .................. 623/23.66; 623/23.64; 623/23.65; 623/23.67

(58) Field of Classification Search
CPC ... A61F 2/04; A61F 2002/047; A61F 2/0022; A61F 2/042; A61F 2/88; A61F 2/94; A61F 2002/048; A61F 2/0031; A61F 2/047; A61F 2/0004
USPC ................. 623/23.68, 23.7, 1.3, 23.64–23.67; 604/8
See application file for complete search history.

(56) References Cited

U.S. PATENT DOCUMENTS

| 4,225,979 A | 10/1980 | Rey et al. |
| 4,307,723 A | 12/1981 | Finney |
| 4,334,327 A | 6/1982 | Lyman et al. |
| 4,643,716 A * | 2/1987 | Drach .............................. 604/8 |
| 4,790,809 A | 12/1988 | Kuntz |
| 4,950,228 A * | 8/1990 | Knapp et al. ...................... 604/8 |
| 5,019,102 A * | 5/1991 | Hoene .......................... 623/23.66 |
| 5,052,998 A | 10/1991 | Zimmon |
| 5,141,502 A * | 8/1992 | Macaluso, Jr. ................ 604/528 |
| 5,306,300 A * | 4/1994 | Berry ........................ 623/23.64 |

(Continued)

FOREIGN PATENT DOCUMENTS

| DE | 19806507 A1 | 8/1999 |
| WO | WO 02/098500 A1 | 12/2002 |

OTHER PUBLICATIONS

International Search Report and Written Opinion for PCT/US08/63581, mailed on Feb. 3, 2009; 17 pages.

(Continued)

*Primary Examiner* — Thomas J Sweet
*Assistant Examiner* — Seema Mathew

(57) ABSTRACT

A stent according to an embodiment of the invention includes an elongate body having a proximal end portion and a distal end portion. The elongate body defines a lumen and an opening in communication with the lumen between the proximal end portion and the distal end portion configured to enable the flow of fluid therethrough. The lumen is configured to have a diameter wherein the opening has a width greater than half the size of the diameter and less than the diameter of the lumen. The opening has a length at least twice the width of opening. In some embodiments, the opening is configured to laterally receive a guidewire therethrough. The elongate body can be configured to releasably couple the guidewire within the lumen of the elongate body such that the elongate body can be slidably moved along the guidewire.

28 Claims, 12 Drawing Sheets

(56) References Cited

U.S. PATENT DOCUMENTS

| | | | |
|---|---|---|---|
| 5,599,291 A * | 2/1997 | Balbierz et al. ............... 604/8 |
| 5,647,843 A * | 7/1997 | Mesrobian et al. ............. 604/8 |
| 5,651,767 A * | 7/1997 | Schulman et al. ............. 604/8 |
| 5,681,274 A * | 10/1997 | Perkins et al. ............... 604/8 |
| 5,766,209 A | 6/1998 | Devonec |
| 5,782,916 A | 7/1998 | Pintauro et al. |
| 5,795,319 A * | 8/1998 | Ali ............................... 604/8 |
| 5,964,744 A | 10/1999 | Balbierz et al. |
| 5,971,967 A | 10/1999 | Willard |
| 5,984,965 A | 11/1999 | Knapp et al. |
| 5,989,207 A * | 11/1999 | Hughes ........................ 604/8 |
| 6,063,119 A | 5/2000 | Pintauro et al. |
| 6,071,292 A | 6/2000 | Makower et al. |
| 6,132,364 A | 10/2000 | Rottenberg et al. |
| 6,168,614 B1 | 1/2001 | Andersen et al. |
| 6,214,037 B1 | 4/2001 | Mitchell et al. |
| 6,524,268 B2 * | 2/2003 | Hayner et al. ............... 604/8 |
| 6,709,465 B2 | 3/2004 | Mitchell et al. |
| 6,908,447 B2 | 6/2005 | McWeeney et al. |
| 6,929,664 B2 * | 8/2005 | Kolb ........................ 623/23.66 |
| 7,041,139 B2 * | 5/2006 | Bluni et al. ............... 623/23.66 |
| 7,182,745 B2 * | 2/2007 | Desmond, III ............... 604/8 |
| 7,217,250 B2 * | 5/2007 | Kolb ........................... 604/8 |
| 7,316,663 B2 * | 1/2008 | Whitmore, III ............... 604/8 |
| 7,338,530 B2 * | 3/2008 | Carter et al. ............... 623/23.66 |
| 7,731,676 B2 * | 6/2010 | Maeda ........................ 604/8 |
| 7,972,292 B2 * | 7/2011 | Behl et al. ................... 604/8 |
| 7,996,976 B2 * | 8/2011 | Desmond, III ................ 29/428 |
| 8,007,540 B2 * | 8/2011 | Robertson .................. 623/23.64 |
| 8,007,702 B2 * | 8/2011 | Gellman ...................... 264/145 |
| 8,398,705 B2 * | 3/2013 | Mangiardi .................. 623/1.15 |
| 2001/0053936 A1 | 12/2001 | Whitmore, III |
| 2003/0195456 A1 * | 10/2003 | Robertson ..................... 604/8 |
| 2004/0181186 A1 * | 9/2004 | Gellman et al. ............... 604/8 |
| 2005/0060023 A1 | 3/2005 | Mitchell et al. |
| 2005/0125072 A1 | 6/2005 | Kolb |
| 2009/0156977 A1 * | 6/2009 | Daignault et al. ............. 604/8 |
| 2010/0179666 A1 * | 7/2010 | Amos, Jr. .................. 623/23.66 |

OTHER PUBLICATIONS

Communication Relating to the Results of the Partial International Search for International Patent Application No. PCT/US03/11879, 4 pages.

International Search for International Patent Application No. PCT/US03/11879, 7 pages.

* cited by examiner

OPEN LUMEN STENT

CROSS-REFERENCE TO RELATED APPLICATIONS

This application claims priority to U.S. Provisional Application Ser. No. 60/917,799, entitled "Open Lumen Stent," filed May 14, 2007, the disclosure of which is hereby incorporated by reference in its entirety.

BACKGROUND

This invention relates to a medical device and more particularly to an open lumen ureteral stent having reduced mass.

Known ureteral stents are typically placed within a urinary tract of a patient to, for example, assist with urinary flow from the kidney to the bladder, or help support a damaged or weakened ureter. Typically, such stents are longitudinally backloaded onto a guidewire to enable insertion and placement of the stent. Backloading of a stent onto a guidewire can require significant time and effort by the physician. Additionally, known ureteral stents often cause discomfort to the patient once the ureteral stents are positioned within the body due to the size and mass of the stent. Some ureteral stents include one or more retention members that further add to the mass of the stent. Such retention members can be positioned within a ureter, bladder and/or kidney of a patient to help retain the ureteral stent in place within the urinary tract of the patient. The large mass of some retention members may not easily conform to the bladder when the bladder is emptied or collapsed, which can result in patient discomfort. Further discomfort can also result when the ureteral stent is removed from a patient due to the size and configuration of the stent and/or retention member.

Thus, a need exists for a ureteral stent having reduced mass that is sufficiently strong to allow urinary flow therethrough. There is also a need for a stent that can laterally receive a guidewire through an opening in the stent to assist in placement of the stent.

SUMMARY OF THE INVENTION

A stent according to an embodiment of the invention includes an elongate body having a proximal end portion and a distal end portion. The elongate body defines a lumen and an opening in communication with the lumen between the proximal end portion and the distal end portion. The lumen is configured to enable the flow of fluid therethrough. The opening has a width greater than half the size of a diameter of the lumen and less than the diameter of the lumen. The opening also has a length at least twice the width of the opening. In some embodiments, the opening is configured to laterally receive a guidewire therethrough. The elongate body can be configured to releasably couple the guidewire within the lumen of the elongate body such that the elongate body can be slidably moved along the guidewire.

BRIEF DESCRIPTION OF THE DRAWINGS

The present invention is described with reference to the accompanying drawings.

DETAILED DESCRIPTION

The medical devices described herein can be inserted into a body lumen of a patient, such as, for example, a urinary tract. For example, a medical device can be configured as a urinary stent that defines a lumen to enable the flow of urine therethrough. A medical device according to an embodiment of the invention can define a lumen and an opening in communication with the lumen. The opening can be defined between a proximal end and distal end of the medical device, and in some embodiments can extend the entire length of the medical device. In such an embodiment, the opening can laterally receive a guidewire therethrough. The medical devices described herein can provide a stent that has reduced mass and increased patient comfort. In some embodiments, an opening defined by the medical device extends through retention members disposed at ends of the medical device, which provides more flexibility of the retention members and further reduces the mass of the device.

In one embodiment, a stent includes an elongate body having a proximal end portion and a distal end portion. The elongate body defines a lumen and an opening in communication with the lumen between the proximal end portion and distal end portion allowing fluid flow therethrough. The opening has a width greater than half the size of a diameter of the lumen and less than the diameter of the lumen. The opening also has a length at least twice the width of the opening. In another embodiment, a ureteral stent includes an opening that extends from a proximal end to a distal end of the elongate body. The opening is configured to laterally receive a guidewire therethrough. The elongate body is configured to releasably couple the guidewire within a lumen of the elongate body such that the elongate body can be slidably moved along the guidewire.

Figure 1:
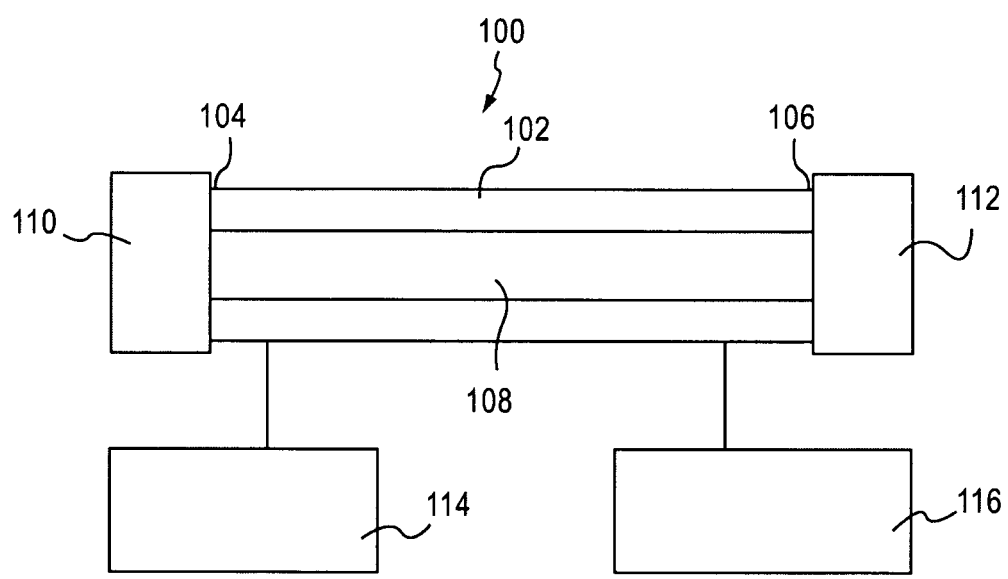
FIG. 1 is a schematic illustration of a medical device according to an embodiment of the invention.

FIG. 1 is a schematic illustration of a medical device according to an embodiment of the invention. A ureteral stent 100 (also referred to herein as "stent") can be placed or otherwise inserted into a body lumen of a patient (not shown in FIG. 1), such as a urinary tract. The stent 100 can extend, for example, from a kidney to a bladder, or from a location in a ureter to a bladder, or from a kidney to a location in a ureter. The stent 100 can be implanted into the urinary tract of the patient by inserting the stent 100 into the patient transurethrally. Alternatively, the ureteral stent 100 can be implanted into the urinary tract of the patient transdermally or percutaneously, such as through the kidney of a patient.

The stent 100 includes an elongate body 102 having a proximal end portion 104 and a distal end portion 106 and defines a lumen (not shown in FIG. 1) between the proximal end portion 104 and the distal end portion 106. The elongate body 102 also defines at least one opening 108 in communication with the lumen. The opening 108 is disposed along a wall of the elongate body 102 between the proximal end portion 104 and the distal end portion 106 of the elongate body 102. The elongate body 102 can also define openings (not shown) on a distal end and a proximal end of the elongate body 102. The lumen works in conjunction with the opening 108 to permit fluid flow, such as urine, through the stent 100 when the stent is disposed, for example, within a urinary tract of a patient. The lumen can be a variety of different shapes and sizes. For example, the lumen can have a cross-sectional shape that is substantially circular, rectangular, square, triangular, etc.

The opening 108 can extend along a portion of the elongate body 102 or extend from the proximal end to the distal end of the elongate body 102. In some embodiments, where there are more than one openings 108, the openings 108 can be defined at spaced locations along a length of the elongate body 102. In some embodiments, the opening 108 can have a width greater than a radius of the lumen, but less than a diameter of the lumen. The opening 108 can also have a length at least twice its width.

The opening(s) 108 reduce the overall mass of the stent 100 to provide improved patient comfort and facilitate fluid flow through the stent 100. In some embodiments, where the opening 108 extends the entire length of the elongate body 102 (e.g., from the proximal end to the distal end), a guidewire 116 can be laterally received through the opening 108 and releasably coupled within the lumen of the elongate body 102. For example, the portions of the elongate body 102 bounding the opening 108 can flex to allow the insertion of the guidewire 116 therethrough. Once the guidewire 116 is disposed within the lumen of the stent 100, the portions of the elongate body 102 bounding the opening 108 return to a non-flexed configuration and retain the guidewire 116 within the lumen of the elongate body 102. The elongate body 102 can slidably move along the guidewire 116 to be placed into a desired position within a body lumen of a patient, such as within a urinary tract of the patient via a pusher device 114. Alternatively, the stent 100 may be backloaded onto the guidewire 116 longitudinally and directed into the desired position within the urinary tract of the patient via the pusher device 114. After placement of the stent 100, the guidewire 116 can be removed from the patient. The pusher 114 can be removed from the guidewire 116 either before or after removing the guidewire 116 from the patient.

The stent 100 can also include one or more retention members configured to retain or anchor the stent 100 within a body lumen of a patient, such as within a urinary tract. A retention member 110 can be disposed at the proximal end portion 104 and/or a retention member 112 can be disposed at the distal end portion 106. The retention members 110 can be used, for example, to help retain the stent 100 within a bladder or ureter of a patient, and the retention member 112 can be used, for example, to help retain the stent 100 within a kidney, or ureter of the patient. The retention members 110 and 112 can be coupled to, or formed integrally with the elongate body 102. The retention members 110 and 112 can have a cross-section substantially the same as, or different from the elongate body 102 and the same as or different than each other. The retention members 110 and 112 can have a variety of different shapes, sizes and configurations including for example, J-shaped, coiled or pigtail-shaped, or any other known configuration for retention of a stent within a body lumen. The retention members 110, 112 can also be expandable, for example, when exposed to fluid within a body lumen.

The elongate body 102 can have a variety of different cross-sectional profiles, and can have different cross-sectional configurations at different locations along a length of the elongate body 102. The elongate body 102 can also define one or more channels (not shown in FIG. 1) disposed along an outer surface of the elongate body 102 to further reduce the mass of the stent and thereby further increase patient comfort. The channels can also increase the amount of fluid flow through the stent 100. The channels can extend from the proximal end to the distal end of the elongate body 102. In some embodiments, the channels may only extend along a portion of the elongate body 102.

As stated above, the pusher device 114 (also referred to herein as "pusher") can be used to insert the stent 100 within a body lumen of a patient. The pusher 114 can have a similar configuration as the stent 100. For example, the pusher device 114 can include an elongate body that defines a lumen (not shown in FIG. 1) and an opening (not shown in FIG. 1) in communication with the lumen along a longitudinal length of the pusher device, as will be described in more detail below. Like the stent 100, the opening defined by the pusher 114 can have a width greater than a radius of the lumen, but less than a diameter of the lumen. The opening of the pusher 114 can also have a length extending from a proximal end to a distal end of the pusher 114. The pusher 114 can be configured to retain a guidewire within a lumen of the pusher 114. In some embodiments, the pusher device 114 includes one or more tab portions located at spaced locations along the length of the pusher 114 that can retain a guidewire within the lumen of the pusher 114. For example, the pusher 114 can include a tab portion at a distal end, a middle portion, and a proximal end. The tab portions can retain the guidewire within the lumen of the pusher 114 as will be described in more detail below. As discussed above, the pusher 114 can slidably move along a guidewire to place the stent 100 into a desired position within the urinary tract of the patient.

Having described above various general principles, several exemplary embodiments of these concepts are now described. These embodiments are only examples, and many other configurations of a medical device and its various components are contemplated by the principles of the invention, and will be apparent to the artisan in view of the general principles described above and the exemplary embodiments. In addition, various other methods and medical procedures can be performed using the medical devices described herein.

FIGS. 2-6 illustrate a medical device according to an embodiment of the invention. A stent 200 includes an elongate body 202 having a proximal end portion 204, a distal end portion 206 and defines a lumen 218 between the proximal end portion 204 and the distal end portion 206. The elongate body 202 also defines an opening 208 in communication with the lumen 218. In this embodiment, the lumen 218 is substantially circular, however, it should be understood that the lumen can be any of a variety of different shapes and configurations, including for example, square, triangular, oval, etc.

Figure 2:
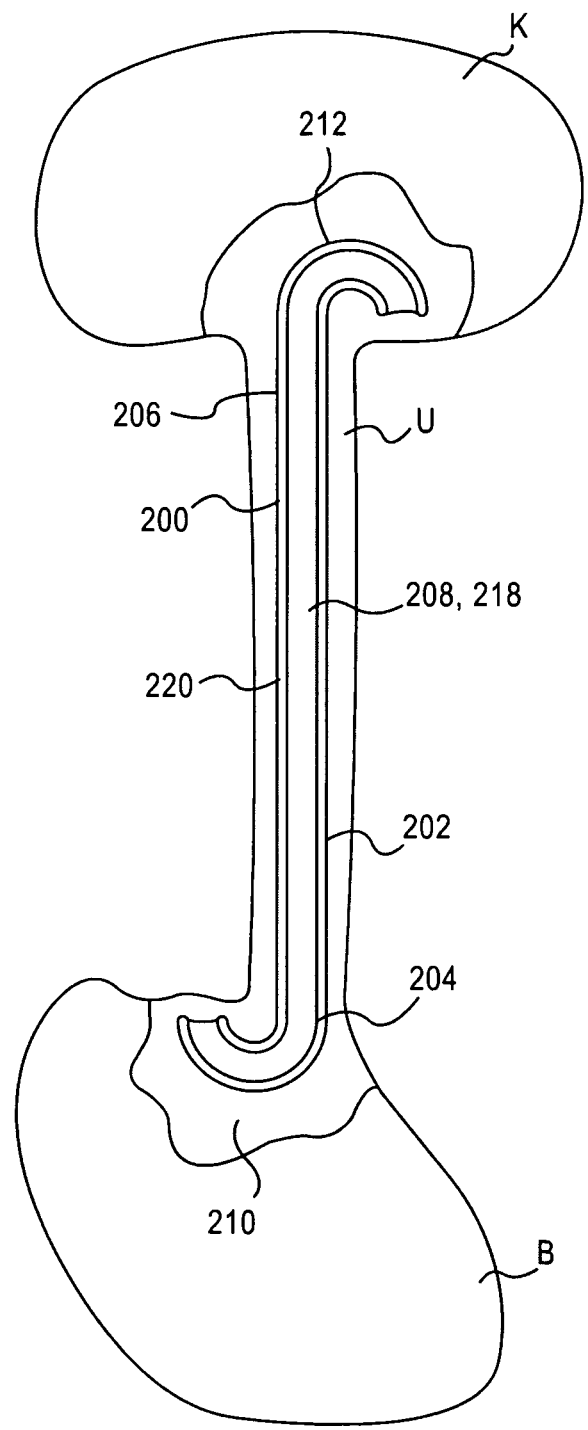
FIG. 2 is a side view of a medical device according to an embodiment of the invention shown positioned within a urinary tract.

The stent 200 also includes a retention member 210 associated with the proximal end portion 204, and a retention member 212 associated with the distal end portion 206. The retention members 210 and 212 are substantially J-shaped, but other configurations can alternatively be used. In this embodiment, the retention members 210, 212 are formed integral with the elongate body 202. As shown in FIG. 2, the elongate body 202 can be disposed within a urinary tract of a patient such that the proximal retention member 210 is disposed within a bladder B, and the distal retention member 212 is disposed within a kidney K.

In this embodiment, the opening 208 and lumen 218 extend between a proximal end and a distal end along the entire length of the elongate body 202 including the retention members 210, 212, as shown in FIG. 2. Thus, a cross-section of the proximal retention member 210 and the distal retention member 212 is substantially the same as a cross-section of a middle portion 220 of the elongate body 202. As shown in the cross-sectional view of FIG. 3, a width W of the opening 208 is greater than a radius R of the lumen 218, but less than a diameter D of the lumen 218. The width of the opening and the diameter of the lumen can be sized such that a guidewire 216, can be received through the opening and disposed within the lumen of the stent. For example, in some embodiments, a diameter of the lumen 218, can be, 0.037 inches (0.940 mm) and the width of the opening 208 can be, for example, 0.034 inches (0.863 mm). Such a stent can be used with a guidewire 216 having an outer diameter of, for example, 0.035 inches (0.889 mm). In other embodiments, a diameter of the lumen 218 can be, for example, 0.027 inches (0.685 mm) for use with a guidewire 216 having an outer diameter, for example, of 0.025 inches (0.635 mm); or a diameter of the lumen 218 can be, for example, 0.040 inches (1.0 mm) for use with a guidewire having an outer diameter of, for example, 0.038 inches (0.9652 mm). As stated previously, the opening 208 reduces the mass of the stent, and thereby decreases the invasiveness of the stent 200, and increases patient comfort.

Figure 4:
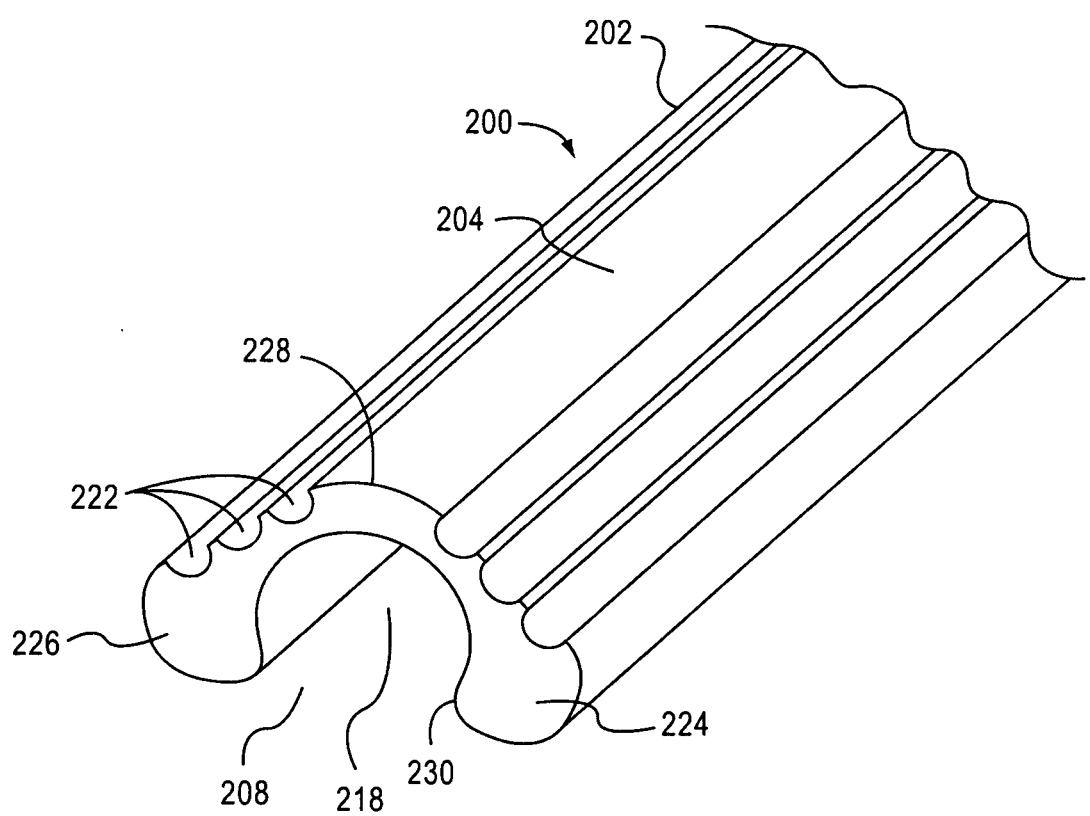
FIG. 4 is a side perspective view of a distal end portion of the medical device of FIG. 2 shown in a straightened configuration.

FIG. 4 is a perspective view of the proximal end portion 204 of the stent 200 shown in a straightened or constrained configuration (i.e., prior to the retention member 210 being allowed to curl). As shown in FIG. 4, the elongate body 202 defines multiple channels 222 that extend along an outside surface of the elongate body 202. The channels 222 can have a variety of shapes and sizes, and can extend the entire length of the stent or only along a portion of the stent. In this embodiment, the channels 222 extend the entire length of the stent including through the retention members 210 and 212. The channels 222 further reduce the mass of the stent 200 and increase the flow of fluid therethrough.

Figure 3:
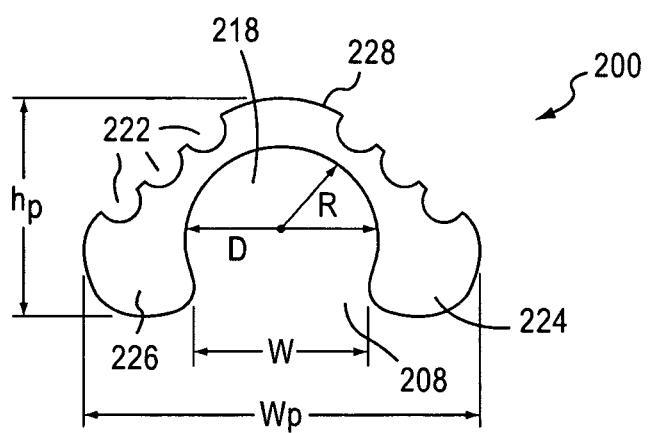
FIG. 3 is a cross-sectional view of the medical device of FIG. 2.

As shown in FIGS. 3 and 4, the elongate body 202 has a cross-sectional profile that includes a first end portion 224 and a second end portion 226 bounding the opening 208, and a middle portion 228. In this embodiment, the channels 222 are disposed between the first end portion 224 and the middle portion 228, and the second end portion 226 and the middle portion 228. The middle portion 228 provides a strengthening beam along the length of the elongate body 202. The first end portion 224 and the second end portion 226 have a wall thickness greater than a wall thickness of the middle portion 228 and each define a lip portion 230 that can be used to releasably couple a guidewire to the elongate body 202 as described in more detail below. As shown in the cross-sectional profile of FIG. 3, the elongate body 202 has a height hp and a width $w_p$. In some embodiments, the height hp and the width $w_p$ can be, for example, 0.040 in (1.016 mm) and 0.075 in (1.905 mm), respectively.

Figure 5:
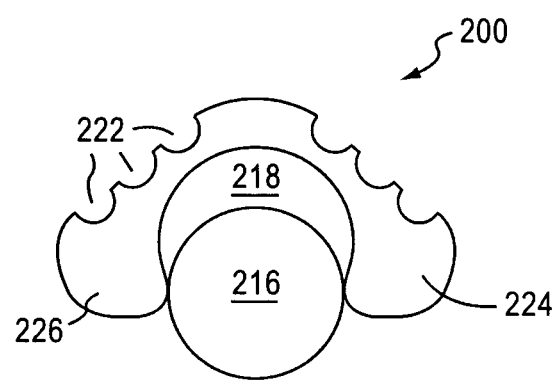
FIG. 5 is a cross-sectional view of the medical device of FIG. 2 shown with a guidewire being disposed through an opening of the medical device.
Figure 6:
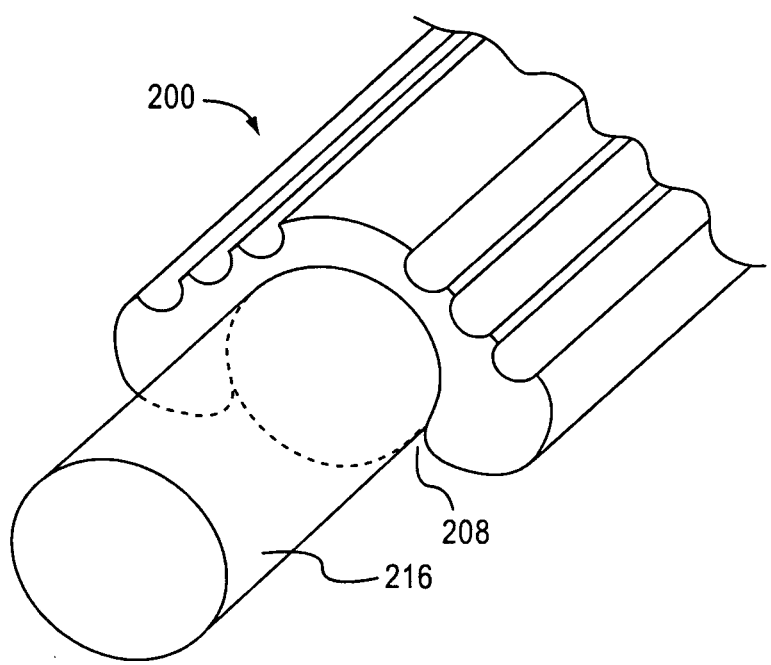
FIG. 6 is a side perspective view of a portion of the medical device of FIG. 2 shown with a guidewire disposed within a lumen of the medical device.

As stated previously, the stent 200 can be laterally loaded onto a guidewire 216 for insertion into a body lumen. For example, a guidewire 216 can be placed within a body lumen of a patient and then the stent 200 can be placed on the guidewire 216 by laterally passing the guidewire 216 through the opening 208 of the stent 200. FIG. 5 is a cross-sectional view illustrating the lateral insertion of the guidewire 216 through the opening 208 of the stent 200. The stent 200 is flexible or bendable such that the end portions 224 and 226 that bound the opening 208 can flex to permit the lateral insertion of the guidewire 216 into the lumen 218. Once inserted and disposed within the lumen 218, the width W of the opening 208 will return substantially to its original size as shown in FIG. 6. The lip portions 230 of the end portions 224 and 226 retain the guidewire within the lumen 218.

Figure 7:
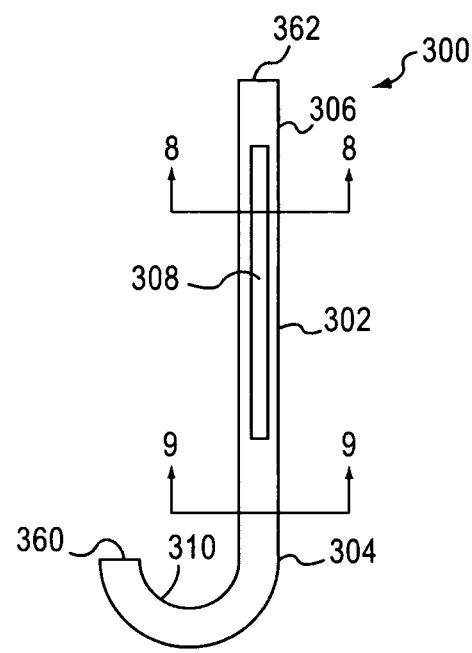
FIG. 7 is a side view of a medical device according to an embodiment of the invention.
Figure 8:
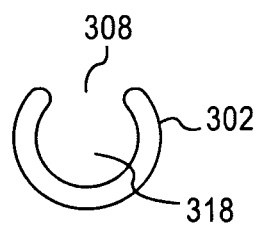
FIG. 8 is a cross-sectional view of the medical device of FIG. 7, taken along the line 8-8 in FIG. 7.
Figure 9:
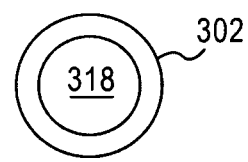
FIG. 9 is a cross-sectional view of the medical device of FIG. 7, taken along the line 9-9 in FIG. 7.

FIGS. 7-9 illustrate a medical device according to another embodiment of the invention. FIG. 7 is a side view of a stent 300 that includes an elongate body 302 having a proximal retention member 310 at a proximal end portion 304, and a distal end portion 306. The elongate body 302 also defines a lumen 318 (shown in FIGS. 8 and 9) between a proximal end 360 and a distal end 362 of the elongate body. The elongate body 302 also defines an opening 308 in communication with the lumen that extends along a portion of a length of the elongate body 302. The opening 308 has a length greater than twice its width. FIG. 8 is a cross-sectional view taken along line 8-8, and FIG. 9 is a cross-sectional view taken along line 9-9, each illustrating the different cross-sectional profiles of the respective portions of the elongate body 302. As with the previous embodiment, the opening 308 helps reduce the overall mass of the stent 300.

Figure 10:
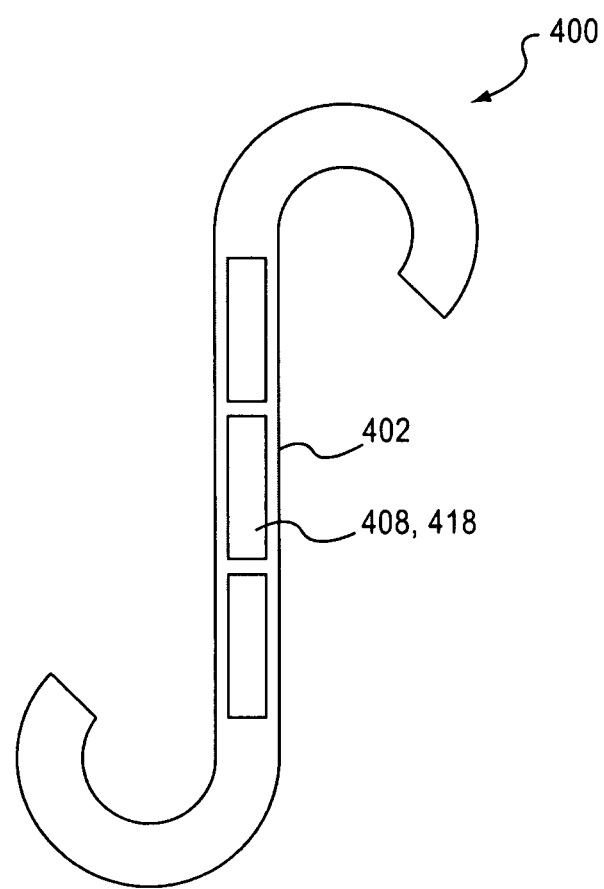
FIG. 10 is a side view of a medical device according to another embodiment of the invention.

FIG. 10 is a side view of a stent 400 including an elongate body 402 that defines multiple openings 408 in communication with a lumen 418. The openings 408 are defined at spaced locations along the elongate body 402. Each of the openings 408 has a width greater than the radius of the lumen 418, but less than the diameter of the lumen 418. The openings 408 also have a length at least twice its width. The openings 408 reduce the mass of the stent 400, and the portions of the elongate body 402 between the openings 408 provide strength to the stent 400.

Figure 11:
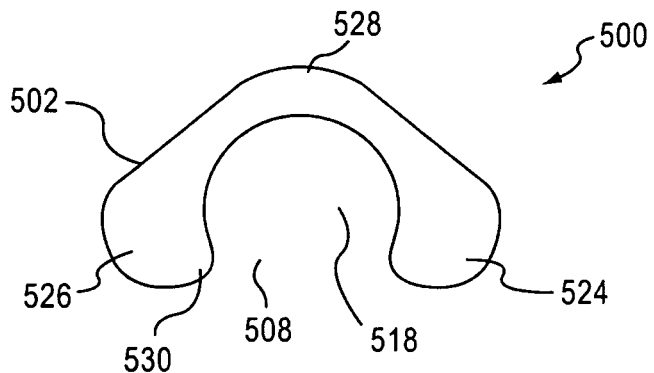
FIGS. 11-13 are cross-sectional views of various embodiments of a medical device according to the invention.
Figure 12:
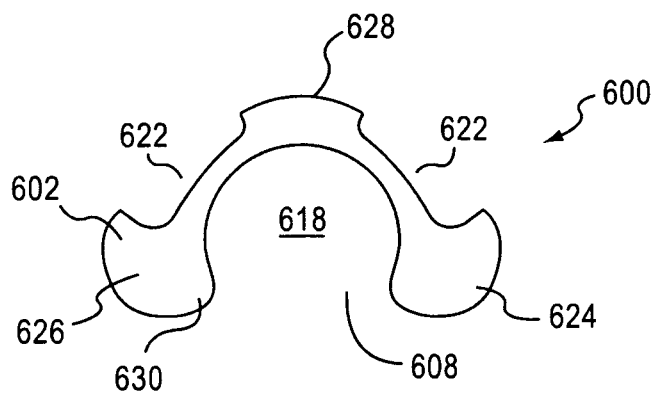
Figure 13:
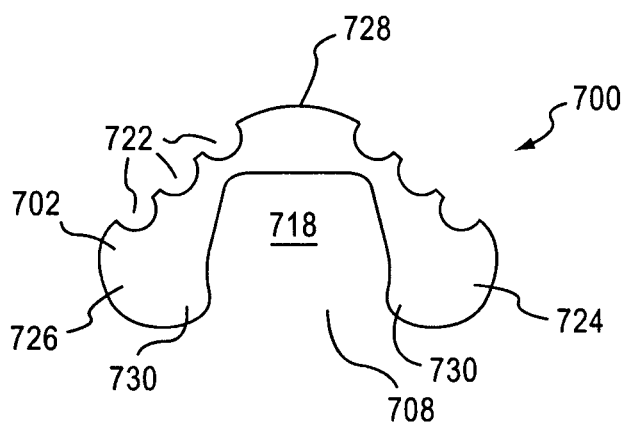

FIGS. 11-13 are cross-sectional views of embodiments of a medical device or stent according to various embodiments of the invention. In each of these embodiments, the stent described can be used in the same manner as described above for previous embodiments. In addition, the features and characteristics of an opening and a lumen defined by an elongate body can be the same as previously described. FIG. 11 illustrates a stent 500 having an elongate body 502 that defines a lumen 518 and an opening 508. This embodiment illustrates an elongate body that does not define channels on an exterior surface thereof. The elongate body 502 has a first end portion 524 and a second end portion 526 that bound the opening 508, and a middle portion 528. The first end portion 524 and the second end portion 526 each have a lip portion 530 to releasably couple a guidewire (not shown in FIG. 11) to the elongate body 502 as described above.

A stent 600 illustrated in FIG. 12, includes an elongate body 602 that defines a lumen 618, and an opening 608. In this embodiment, the elongate body 602 defines a channel 622 disposed between a first end portion 624 and a middle portion 628, and another channel 622 disposed between the second end portion 626 and the middle portion 628. In another embodiment, shown in FIG. 13, a stent 700 includes an elongate body 702 that defines a lumen 718 that has a rectangular cross-section. The elongate body 702 also defines multiple channels 722 disposed between a first end portion 724 and a middle portion 728, and a second end portion 726 and the middle portion 728. The middle portions 628, 728 of FIGS. 12 and 13 provide a strengthening beam along the length of the respective elongate body 602, 702. The first end portion 524, 624, 724 and the second end portion 526, 626, 726 each have a wall thickness greater than a wall thickness of the middle portion 528, 628, 728 and each define a lip portion 530, 630, 730 that can be used to releasably couple a guidewire (not shown in FIGS. 11-13) to the elongate body 502, 602, 702 as described above.

Figure 14:
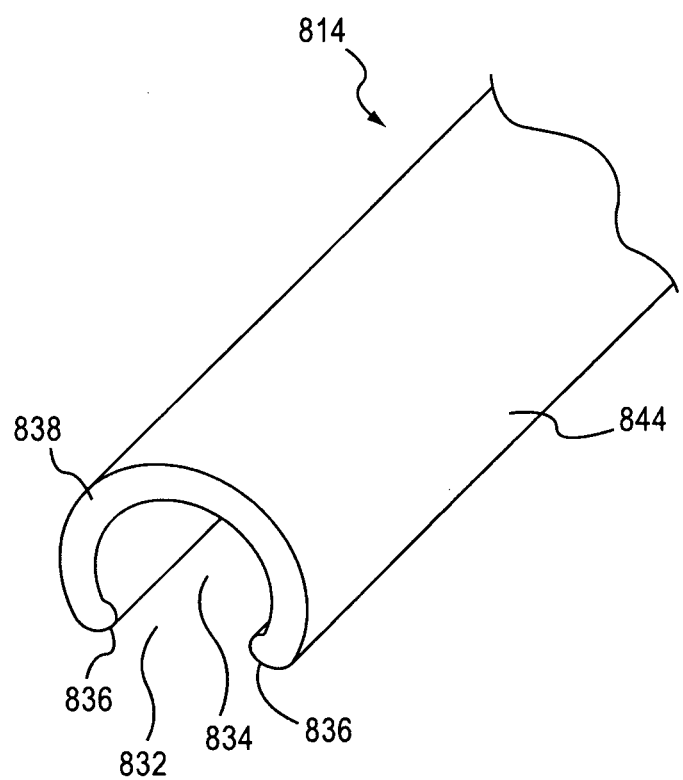
FIG. 14 is a side perspective view of a portion of a pusher device according to an embodiment of the invention.
Figure 15:
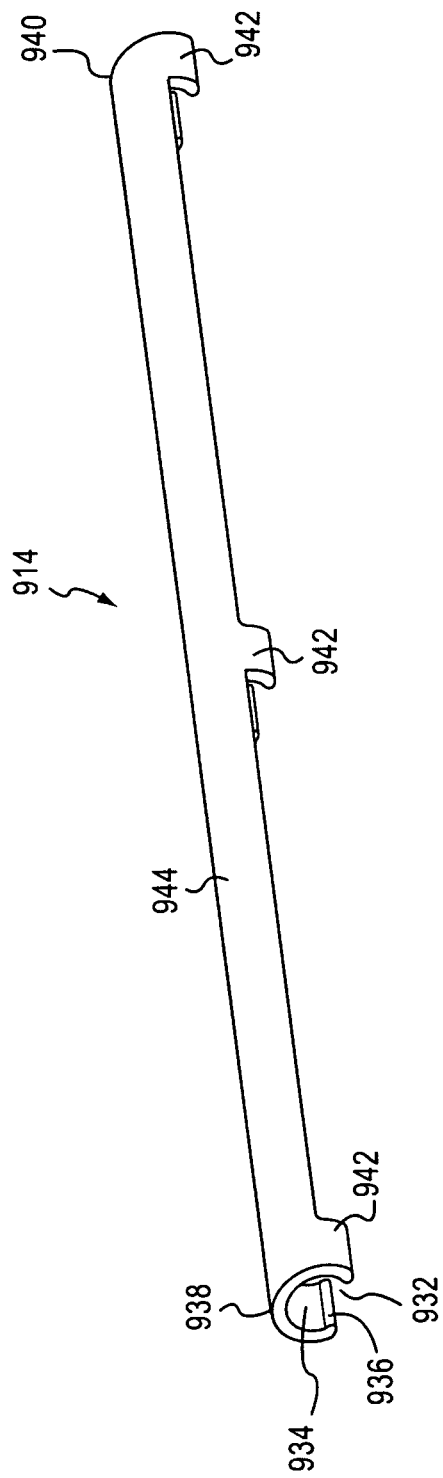
FIG. 15 is a side perspective view of a pusher device according to another embodiment of the invention.

FIGS. 14 and 15 illustrate a medical device according to another embodiment of the invention. FIG. 14 is a perspective view of a pusher 814 that includes an elongate body 844 having a proximal end portion 838 and a distal end portion (not shown in FIG. 14). The elongate body 844 defines a lumen 834 and an opening 832 in communication with the lumen 834 between a proximal end and a distal end of the pusher 814. As with the stents described above, the opening 832 has a width greater than a radius of the lumen 834, and less than a diameter of the lumen 834. A first end portion and a second end portion each define a lip portion 836 used to releasably couple a guidewire (not shown in FIG. 14) to the elongate body 844.

In an alternative embodiment, shown in FIG. 15, a pusher 914 includes an elongate body 944 that defines a lumen 934 and an opening 932, and includes a pair of tabs 942 at spaced locations along a length of the elongate body 944. The tabs 942 can be used to couple the pusher 914 to a guidewire. As shown in FIG. 15, the tabs 942 are positioned at the proximal end portion 938, the distal end portion 940, and at a mid-point of the elongate body 944. In other embodiments, tabs can be disposed at different locations, and a different number of tabs can be included. A size of the opening 932 defined at the tabs 942 is less than a size of the opening 932 throughout the remaining portion of the elongate body 944. This configuration provides further reduction in the total mass of the pusher 914. Each tab 942 defines a lip portion 936 used to releasably couple a guidewire (not shown in FIG. 15) to the elongate body 944. As with the stent 200, the end portions and/or tabs 942 that bound the openings 832 and 932 of pushers, 814 and 914 have the ability to flex to permit the lateral insertion of a guidewire. Once inserted, the lip portions 836, 936, retain the guidewire within the pusher 814, 914.

Figure 16:
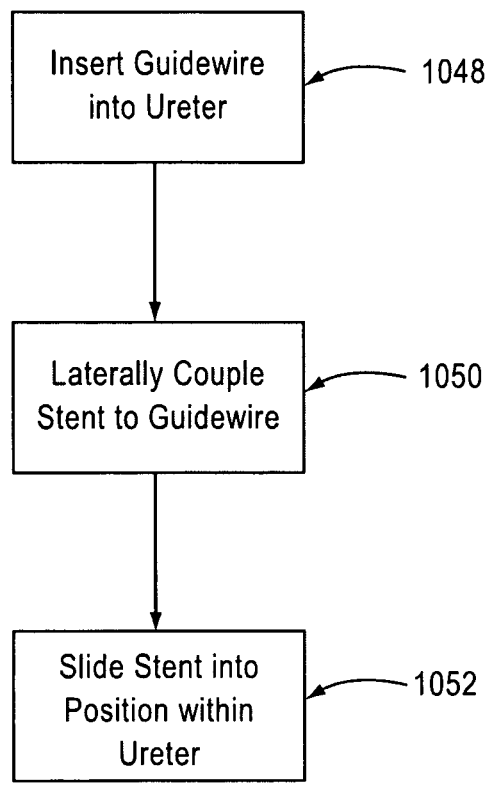
FIG. 16 is a flowchart illustrating a method according to an embodiment of the invention.

FIG. 16 is a flowchart of a method according to an embodiment of the invention. A method includes at 1048 transurethrally inserting a guidewire (e.g., 116, 216) into a ureter of a patient. At 1050, the portion of the guidewire disposed outside of the patient is coupled to a stent (e.g., 200) by disposing the guidewire laterally through an opening defined by the stent and into a lumen of the stent. For example, the opening can extend along the length of the stent and be in communication with the lumen. At 1052, the stent can be slidably moved along the guidewire to a position where at least a portion of the stent is within the ureter of the patient using, for example, a pusher (e.g., 814, 914). In some embodiments, a pusher is also coupled to the guidewire by disposing the guidewire laterally through an opening defined by the pusher. The stent can include retention members (e.g., 210, 212) that can be disposed within the kidney and/or bladder of the patient to help retain the stent in position.

The stent (e.g., stent 100, 200, etc.) and pusher (e.g., 814, 914) may be formed from a number of various biocompatible materials used in medical devices. The stent and/or pusher may include one material or may be formed, for example by extrusion, of two or more materials along its length. For example, in one embodiment, a distal end portion of the elongate body can be formed from a first material and the proximal end portion can be formed from a different second material. Accordingly, the proximal end portion may be made of a softer material than that of the distal end portion, and vice versa. Likewise, the retention members (e.g., 110, 112) can be formed with the same or different material than each other and/or the elongate body.

The elongate body and the retention member can be formed from any material or materials known in the art to be used in constructing ureteral stents. One subset of biocompatible materials best suited for the elongate body exhibit at least some of the following characteristics: high tensile strength, high retention coil strength, excellent biocompatibility and biodurability, excellent radiopacity or fluoroscopic visibility, availability in varying durometers, and a low resistance to passage. For example, in one embodiment, the elongate body is formed with a polymeric material.

In some embodiments, a kit can be provided that includes one or more ureteral stent and one or more pusher device as described herein. For example, a kit can include a ureteral stent, such as stent 200, and a pusher, such as pusher 814 or 914. As described above, the stent can define a lumen and an opening in communication with the lumen along at least a portion of a length of the stent. In some embodiments, the stent is configured to laterally receive a guidewire through the opening. Likewise, the pusher can be configured to laterally receive a guidewire through an opening along a length of the pusher. In some embodiments, a kit can also include one or more guidewires used for insertion of the stent into a ureter.

CONCLUSION

While various embodiments of the invention have been described above, it should be understood that they have been presented by way of example only, and not limitation. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

The previous description of the embodiments is provided to enable any person skilled in the art to make or use the invention. While the invention has been particularly shown and described with reference to embodiments thereof, it will be understood by those skilled in art that various changes in form and details may be made. For example, a stent and/or pusher device can include various combinations and sub-combinations of the various embodiments described herein. In addition, a stent can include one or more of the features described with reference to a pusher device, and vice versa. For example, a stent can include tabs as described in the embodiment of a pusher.

What is claimed is:

1. A ureteral stent, comprising:
an elongate body having a proximal end and a distal end and defining a lumen and an opening in communication with the lumen, the opening extending an entire length of the elongate body from the proximal end of the elongate body to the distal end of the elongate body, the elongate body having an inner surface and an outer surface disposed opposite the inner surface, the inner surface defining the lumen, the elongate body defining at least one groove on the outer surface of the elongate body,
the lumen having a diameter, the opening having a width greater than ½ the size of the diameter of the lumen and less than the diameter of the lumen,
the opening having a length at least twice the width of the opening, wherein the elongate body has a cross-sectional profile including a first end portion, a second end portion, and a middle portion between the first end portion and the second end portion, inner surfaces of the first end portion and the second end portion defining the opening, the first and second end portions being enlarged portions each having a thickness greater than the middle portion.

2. The ureteral stent of claim 1, further comprising:
a retention member disposed at least one of the proximal end or the distal end of the elongate body, the retention member configured to help anchor the elongate body within a ureter.

3. The ureteral stent of claim 1, further comprising:
a first retention member at the proximal end of the elongate body and a second retention member at the distal end of the elongate body, the first retention member configured to be disposed within a bladder, the second retention member configured to be disposed within a kidney.

4. The ureteral stent of claim 1, the at least one groove includes a first groove and a second groove, the first groove being disposed on the outer surface of the elongate body between the first end portion and the middle portion, the second groove being disposed on the outer surface of the elongated body between the second end portion and the middle portion.

5. The ureteral stent of claim 1, wherein the opening is configured to laterally receive a guidewire therethrough,
the elongate body being configured to releasably couple the guidewire within the lumen of the elongate body such that the elongate body can be slidably moved along the guidewire.

6. A ureteral stent, comprising:
an elongate body having a proximal end and a distal end and defining a lumen, and an opening in communication with the lumen, the elongate body having an inner surface and an outer surface disposed opposite the inner surface, the inner surface defining the lumen, the elongate body defining a groove on the outer surface of the elongate body, the elongate body having a cross-sectional profile including a first end portion and a second end portion each bounding the opening, and a middle portion between the first end portion and the second end portion, the first end portion and the second end portion being enlarged portions each having a wall thickness greater than a wall thickness of the middle portion of the elongate body,
the proximal end including a curved retention portion,
the distal end including a curved retention portion,
the opening extending from the proximal end of the elongate body to the distal end of the elongate body,
the opening configured to laterally receive a guidewire therethrough,
the elongate body being configured to releasably couple the guidewire within the lumen of the elongate body such that the elongate body can be slidably moved along the guidewire.

7. The ureteral stent of claim 6, wherein the groove including a plurality of first grooves and a plurality of second grooves, the plurality of first grooves being disposed on the outer surface of the elongate body between the first end portion and the middle portion, the plurality of second grooves being disposed on the outer surface of the elongate body between the second end portion and the middle portion.

8. The ureteral stent of claim 7, wherein the plurality of first grooves are equally spaced apart, and the plurality of second grooves are equally spaced apart.

9. The ureteral stent of claim 6, wherein the lumen has a diameter, the opening has a width greater than ½ the size of the diameter of the lumen and less than the diameter of the lumen.

10. A ureteral stent, comprising:
an elongate body having a proximal end and a distal end and defining a lumen, the elongate body having an inner surface and an outer surface disposed opposite the inner surface,
the elongate body defining at least one groove on the outer surface of the elongate body, the at least one groove extending along an entire length of the elongate body,
the elongate body having a substantially u-shaped cross-sectional profile having a first end portion, a second end portion, and a middle portion between the first end portion and the second end portion,
the elongate body having an interior perimeter bounding the lumen, the first end portion and the second end portion each bounding an opening in communication with the lumen, the opening extending along the entire length of the elongate body, the opening configured to laterally receive a guidewire therethrough, the opening having a width greater than ½ the size of a diameter of the lumen and less than the diameter of the lumen,
the first end portion and the second end portion being enlarged portions each having a wall thickness greater than a wall thickness of the middle portion of the elongate body.

11. The ureteral stent of claim 10, further comprising:
a retention member disposed on at least one of the proximal end or the distal end of the elongate body configured to help retain the elongate body within a ureter.

12. The ureteral stent of claim 10, wherein the opening extends from the proximal end to the distal end of the elongate body.

13. The ureteral stent of claim 10, wherein the opening is configured to laterally receive a guidewire therethrough,
the elongate body being configured to releasably couple the guidewire within the lumen of the elongate body such that the elongate body can be slidably moved along the guidewire.

14. A ureteral stent, comprising:
an elongate body having, a proximal end and a distal end and defining a lumen, and an opening in communication with the lumen, the lumen having a diameter, the elongate body having an inner surface and an outer surface opposite the inner surface, the outer surface of the elongate body defining a channel,
the elongate body has a cross-sectional profile having a first end portion and a second end portion each bounding the opening, and a middle portion,
at least a portion of the elongate body having an overall width measured along the cross-sectional profile from an outer edge of the first end portion to an outer edge of the second end portion, and an overall height measured along the cross-sectional profile in a direction perpendicular to the overall width, the overall width being greater than the height.

15. The ureteral stent of claim 14, wherein the elongate body defines a plurality of channels on the outer surface of the elongate body.

16. The ureteral stent of claim 14, further comprising:
a retention member disposed on at least one of the proximal end or the distal end of the elongate body configured to help retain the elongate body within a ureter.

17. The ureteral stent of claim 14, wherein the opening is configured to laterally receive a guidewire therethrough, the elongate body being configured to releasably couple the guidewire within the lumen of the elongate body such that the elongate body can be slidably moved along the guidewire.

18. The ureteral stent of claim 14, wherein the elongate body has a cross sectional profile having a first end portion and a second end portion each bounding the opening, and a middle portion, the first end portion and the second end portion each having a wall thickness greater than a wall thickness of the middle portion of the elongate body.

19. A kit, comprising:
a ureteral stent defining a lumen and an opening in communication with the lumen, the opening extending along an entire length of the ureteral stent from a proximal end to a distal end of the ureteral stent and being configured to laterally receive a guidewire therethrough, the ureteral stent having a cross-sectional profile including a first end portion, a second end portion, and a middle portion between the first end portion and the second end portion, inner surfaces of the first end portion and the second end portion defining the opening of the ureteral stent, the first and second end portions being enlarged portions each having a thickness greater than the middle portion; and
a pusher device, the pusher device defining a lumen and an opening in communication with the lumen of the pusher device, the og pusher device extending from a proximal end to a distal end of the pusher device and being configured to laterally receive a guidewire therethrough.

20. The kit of claim 19, wherein the distal end of the pusher is configured to engage the proximal end of the ureteral stent and used to insert the ureteral stent into a ureter transurethrally.

21. A method, comprising:
inserting a guidewire transurethrally into a ureter of a patient;
coupling a ureteral stent to a portion of the guidewire disposed outside of the patient by disposing the guidewire in a first direction through an opening defined by the ureteral stent and into a lumen defined by the ureteral stent, the opening defined by the ureteral stent extending along an entire length of the ureteral stent from a proximal end portion of the ureteral stent to a distal end portion of the ureteral stent, the ureteral stent having a cross-sectional profile including a first end portion, a second end portion, and a middle portion between the first end portion and the second end portion, inner surfaces of the first end portion and the second end portion defining the opening of the ureteral stent, the first and second end portions being enlarged portions each having a thickness greater than the middle portion; and
slidably moving the ureteral stent in a second direction along the guidewire to position at least a portion of the ureteral stent within the ureter of the patient, the second direction being substantially perpendicular to the first direction.

22. The ureteral stent of claim 6, further comprising:
a retention member disposed on the proximal end of the elongate body configured to help retain the elongate body within a ureter, the opening extending within the retention member.

23. The ureteral stent of claim 14, wherein the diameter of the lumen is at least 92% of the outer width of the at least a portion of the elongate body.

24. The method of claim 21, wherein the coupling the ureteral stent includes coupling the ureteral stent to a portion of the guidewire at a spaced distance from an end of the guidewire.

25. The ureteral stent of claim 1, wherein the elongate body includes a side wall, the side wall being devoid of a passageway extending through the side wall.

26. The ureteral stent of claim 6, wherein the elongate body includes a side wall, the side wall being devoid of a passageway extending through the side wall.

27. The ureteral stent of claim 1, wherein the proximal end of the elongate body includes a curved retention member and the distal end of the elongate body includes a curved retention member.

28. The ureteral stent of claim 1, wherein the at least one groove extends along the entire length of the elongate body from the proximal end of the elongate body to the distal end of the elongate body.

* * * * *